US00PP09684P

United States Patent [19]

VandenBerg

[11] Patent Number: Plant 9,684

[45] Date of Patent: Nov. 5, 1996

[54] CHRYSANTHEMUM PLANT NAMED 'WHITE MIAMI'

[75] Inventor: Cornelis P. VandenBerg, Salinas, Calif.

[73] Assignee: Yoder Brothers, Inc., Barberton, Ohio

[21] Appl. No.: 547,219

[22] Filed: Oct. 24, 1995

[51] Int. Cl.[6] ..... A01H 5/00

[52] U.S. Cl. ..... Plt./82.1

[58] Field of Search ..... Plt./82.1

[56] References Cited

U.S. PATENT DOCUMENTS 4,616,099 10/1986 Sparkes ..... 47/58

OTHER PUBLICATIONS

Broertjes, et al., 1980, "A mutant of a mutant of a . . . Irradiation of progressive radiation–induced mutants in a mutation breeding programme with *Chrysanthemum morifolium*", Euphytica, 29:525–530.

Gosling, ed., 1979, "The Chrysanthemum Manual–6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by X–rays", Am. Soc. Hort. Sci. Proc., pp. 613–620.

Broertjes, 1966, "Mutation breeding of Chrysanthemums", Euphytica, 15:156–162.

Dowrick, et al., 1966, "The induction of mutations in chrysanthemum using X–and gamma radiation", Euphytica, 15:204–210.

*Primary Examiner*—Howard J. Locker

*Attorney, Agent, or Firm*—Foley & Lardner

[57] ABSTRACT

A chrysanthemum plant named White Miami particularly characterized by its flat capitulum form; daisy capitulum type; white ray floret color; small flowers, with a diameter across face of capitulum of 38 to 41 mm when fully opened, when grown as a single stem spray cut mum; flowering response is 51 to 60 days after start of short days; plant height is 79 to 86 cm when grown with 17 to 18 long days prior to start of short days; peduncle length of both the first and the fourth lateral at flowering after removing the apical bud without growth regulator applications is 5 to 8 cm; high production of flowers per stem, with 14 to 17 laterals developing; top laterals produe one terminal flower, lower laterals produce one terminal flower and 2 to 4 secondary flowers; and recommended as spray cut mum.

1 Drawing Sheet

The present invention comprises a new and distinct cultivar of Chrysanthemum, botanically known as *Dendranthema grandiflora,* and referred to by the cultivar name White Miami.

White Miami, identified as 3661 (90-571B01), is a product of a mutation induction program. The new cultivar was discovered and selected by inventor Cornelis P. VandenBerg on Dec. 10, 1993 in a controlled environment in Salinas, Calif. as one flowering plant within a flowering block established as rooted cuttings from stock plants which had been exposed as unrooted cuttings to an X-ray source of 1750 rads in Fort Myers, Fla. on May 13, 1993. The irradiated parent cultivar was the cultivar Miami, described as a daisy spray cut mum with a very light pink ray floret color with many small flowers. The ray floret color of the parent cultivar Miami was considered to be too light for commercial introduction, and was never introduced nor patented in North America.

The irradiation program resulting in White Miami had as its primary objective the expansion of color ranges of the parent cultivar Miami. The irradiation program comprised irradiation of cuttings of the parent cultivar at irradiation levels of 1500, 1750 and 2000 rads. A total of 2,145 cuttings harvested from a total of 225 irradiated plants were planted on Oct. 4, 1993. Of these, 13 initial selections were made, which selections were then revegetated and reflowered in Honselersdijk, The netherlands. This flowering resulted in discarding 11 of the original 13 selections on Aug. 29, 1994. The remaining wo selections were maintained as PIs (Possible Introductions) and further trialed in Salinas, Calif. and Honselersdijk, The Netherlands, ultimately resulting in the decision to introduce the 2 remaining selections as White Miami and Pink Miami. Pink Miami is disclosed in copending application Ser. No. 08/547397.

The first act of asexual reproduction of White Miami was accomplished when vegetative cuttings were taken from the initial selection in February of 1994 in a controlled environment in Salinas, Calif., by technicians working under supervision of Cornelis P. VandenBerg.

Horticultural examination of controlled flowerings of successive plantings has shown that the unique combination of characteristics as herein disclosed for White Miami are firmly fixed and are retained through successive generations of asexual reproduction.

White Miami has not been observed under all possible environmental conditions. The phenotype may vary significantly with variations in environment such as temperature, light intensity and daylength, without, however, any variance in genotype.

The following observations, measurements and comparisons described plants grown in Salinas, Calif., under greenhouse conditions which approximate those generally used in commercial greenhouse practice.

The following traits have been repeatedly observed and are determined to be basic characteristics of White Miami, which, in combination, distinguish this Chrysanthemum as a new and distinct cultivar:

1. Flat capitulum form.
2. Daisy capitulum type.
3. White ray floret color.
4. Small flowers, with a diameter across face of capitulum of 38 to 41 mm when fully opened, when grown as a single stem spray cut mum.
5. Flowering response is 51 to 60 days after start of short days.
6. Plant height is 79 to 86 cm when grown with b 17to 18 long days prior to start of short days.

7. Peduncle length of both the first and the fourth lateral at flowering after removing the apical bud without growth regulator applications is 5 to 8 cm.

8. High production of flowers per stem, with 14 to 17 laterals developing. Top laterals produce one terminal flower, lower laterals produce one terminal flower and 2 to 4 secondary flowers.

9. Recommended as spray cut mum.

The accompanying photographic drawing is a side view of a single stem cut spray mum of White Miami, with the colors being as nearly true as possible with illustrations of this type.

Of the commercial culivars known to the inventor, the most similar in comparison to White Miami is the parent cultivar Miami. All traits of White Miami are similar to those of Miami, except for the ray floret color. The ray floret color of White Miami is White, while the ray florer color of Miami is a very light pink. When compared with the sister cultivar Pink miami, disclosed in co-pending application Ser. No. 08/547,397, White Miami has a 3 to 5 cm shorter plant height than Pink Miami, while the ray floret color of white Miami is white, compared to the light purple ray floret color of Pink Miami.

In the following description color references are made to the Royal Horticultural Society Colour Chart. The color values were determined on plant material grown as a single stem spray cut mum grown in Salinas, Calif. on Jul. 7, 1995.

Classification:

*Botanical.*—*Dendranthema grandiflora* cv White Miami.

*Commercial.*—Flat daisy spray cut mum.

INFLORESCENCE

A. Capitulum:

*Form.*—Flat.

*Type.*—Daisy.

*Diameter across face.*—38 to 41 mm when fully opened.

B. Corolla of ray florets:

*Color (general tonality from a distance of three meters).*—White.

*Color (upper surface)*:—155B.

*Color (Under surface)*:—155B.

*Shape.*—Longitudinal straight, cross section concave.

C. Corolla of disc florets:

*Color (mature)*:—b 15A.

*Color (immature).*—15 A. overlaid with 144B.

D. Reproductive Organs:

*Androecium.*—Present on disc florets only; no pollen.

*Gynoecium.*—Present on both ray and disc florets.

PLANT

A. General Appearance:

*Height.*—79 to 86 cm when grown in Salinas with 17 to 18 long days prior to start of short days.

B. Foliage:

*Color (upper surface).*—147A.

*Color (under surface).*—147B.

*Shape.*—Deeply lobed, strongly serrated.

What is claimed is:

1. A new and distinct Chrysanthemum plant named White Miami, as described and illustrated.

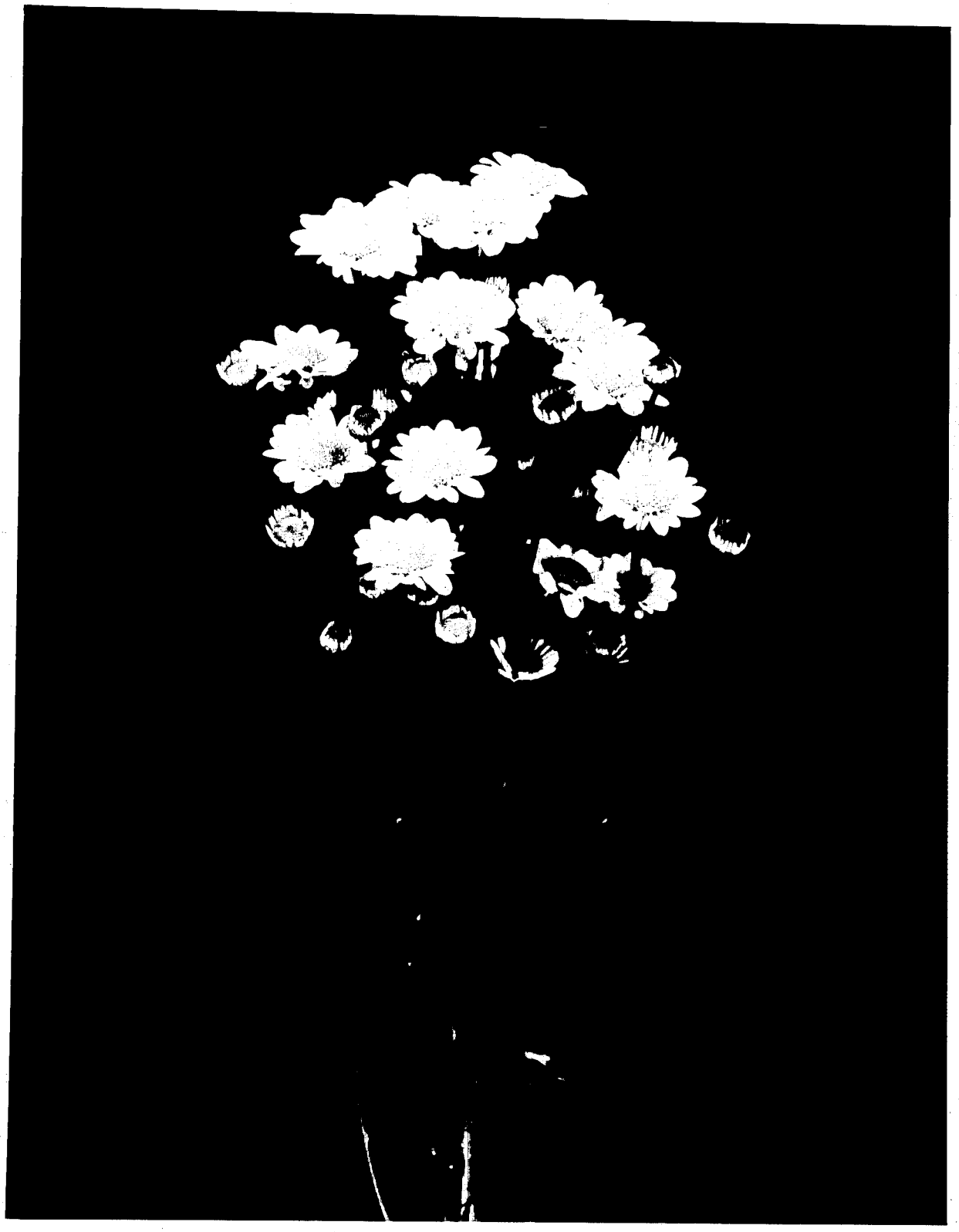

* * * * *